(12) United States Patent
Nakahara et al.

(10) Patent No.: US 6,966,973 B2
(45) Date of Patent: Nov. 22, 2005

(54) APPARATUS AND PROCESS FOR PRODUCING (METH)ACRYLIC ACID

(75) Inventors: Sei Nakahara, Himeji (JP); Kazuhiko Sakamoto, Himeji (JP); Yukihiro Matsumoto, Kobe (JP); Kenji Sanada, Himeji (JP); Masatoshi Ueoka, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 400 days.

(21) Appl. No.: 10/186,569

(22) Filed: Jul. 1, 2002

(65) Prior Publication Data

US 2002/0165407 A1    Nov. 7, 2002

Related U.S. Application Data

(62) Division of application No. 09/735,091, filed on Dec. 12, 2000, now Pat. No. 6,441,228.

(51) Int. Cl.[7] .......................... B01D 3/00; C07C 51/44; B01V 19/00
(52) U.S. Cl. .................... 202/163; 202/267.1; 203/86; 159/DIG. 15; 422/240; 562/600
(58) Field of Search .......................... 202/267.1, 163; 203/86; 159/DIG. 15; 562/600; 422/240; 165/133, 134

(56) References Cited

U.S. PATENT DOCUMENTS

| 3,493,471 A | * | 2/1970 | Bashaw .......................... 203/8 |
| 4,147,885 A | | 4/1979 | Shimizu et al. |
| 4,350,573 A | * | 9/1982 | Kritzler et al. ............... 203/86 |
| 5,087,744 A | | 2/1992 | Krabetz et al. |

FOREIGN PATENT DOCUMENTS

| JP | 63027457 | * | 2/1988 |
| WO | 99/54017 | * | 10/1999 |

OTHER PUBLICATIONS

Klimova edt al, "Corrosion resistance of materials in media for production of the methyl ester of methacrylic acid" Russian.*

* cited by examiner

Primary Examiner—Virginia Manoharan

(57) ABSTRACT

The present invention provides an apparatus for producing (meth)acrylic acid and a process for producing (meth)acrylic acid with this apparatus wherein the apparatus enables the production of (meth)acrylic acid stably for a long period of time by effectively inhibiting the polymerization of (meth) acrylic acid in its production process (for example, in a reboiler). At least a part of the apparatus is made of a nickel-chromium-iron alloy with a molybdenum content of 3 to 20 mass %, but not including 3 mass %, or with a molybdenum content of 1 to 4 mass % and a copper content of 0.5 to 7 mass %.

17 Claims, 1 Drawing Sheet

APPARATUS AND PROCESS FOR PRODUCING (METH)ACRYLIC ACID

Figure 1:
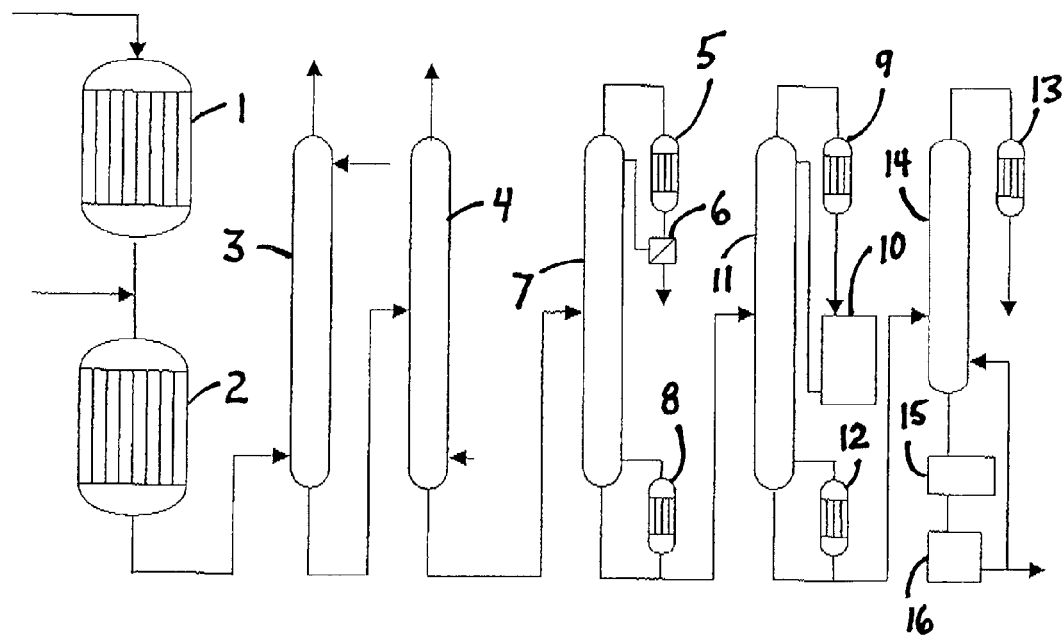

This application is a divisional of U.S. patent application Ser. No. 09/735,091 filed on Dec. 12, 2000 now U.S. Pat. No. 6,441,228 and claims the benefit thereof under 35 U.S.C. § 120.

BACKGROUND OF THE INVENTION

A. Technical field

The present invention relates to an apparatus and a process for producing (meth)acrylic acid.

B. Background Art

It is a general industrial practice to produce (meth)acrylic acid by catalytic gas phase oxidation. However, (meth)acrylic acid is very easily polymerizable. Therefore there is a possibility that its polymerization often might occur in its production process and, as a result, it might become impossible to continue the operation.

Usually, polymerization inhibitors such as hydroquinone, phenothiazine, hydroquinone monomethyl ether, diphenylamine, copper dialkyldithiocarbamates, N-oxyl compounds and molecular-oxygen-containing gases are used in order to inhibit the polymerization of (meth)acrylic acid in its production process, or the inner wall surface of the apparatus is treated in order to prevent solid materials, such as polymers and deposits, from attaching to the apparatus.

However, even the use of the polymerization inhibitor or the inner wall surface treatment for the apparatus still results in insufficient inhibition of the polymerization of (meth)acrylic acid.

SUMMARY OF THE INVENTION

A. Object of the Invention

It is an object of the present invention to provide an apparatus for producing (meth)acrylic acid and a process for producing (meth)acrylic acid with this apparatus wherein the apparatus enables the production of (meth)acrylic acid stably for a long period of time by effectively inhibiting the polymerization of (meth)acrylic acid in its production process.

B. Disclosure of the Invention

SUS316 stainless steel (molybdenum content=2.0 to 3.0 mass %, copper content=0 mass %) is usually used for the apparatus for producing (meth)acrylic acid. However, by the present inventors' studies, it has been found that apparatuses made of stainless steel with a low molybdenum content such as SUS316 are liable to involve the polymerization of (meth)acrylic acid, and that much polymerization occurs particularly in reboilers of distillation columns in which (meth)acrylic acid is exposed to severe conditions, and further that the polymerization of (meth)acrylic acid can effectively be inhibited by replacing the SUS316 with a nickel-chromium-iron alloy having a high molybdenum content or containing copper even if the molybdenum content is low. The present invention has been completed on the basis of such findings.

That is to say, the present invention provides an apparatus for producing (meth)acrylic acid by catalytic gas phase oxidation, wherein at least a part (particularly, a part coming into contact with (meth)acrylic acid) of the apparatus is made of:

(A) a nickel-chromium-iron alloy with a molybdenum content of 3 to 20 mass %, but not including 3 mass %; (in other words, more than 3 times the mass % and not more than 20 mass %); or (B) a nickel-chromium-iron alloy with a molybdenum content of 1 to 4 mass % and a copper content of 0.5 to 7 mass %.

The present invention further provides a process for producing (meth)acrylic acid, in which (meth)acrylic acid is produced with the above apparatus according to the present invention.

These and other objects and the advantages of the present invention will be more fully apparent from the following detailed disclosure.

FIG. 1 is a schematic view of an apparatus for producing (meth)acrylic acid.

DETAILED DESCRIPTION OF THE INVENTION

The apparatus according to the present invention encompasses all apparatuses used in production processes which comprise the steps of mainly producing acrolein from propylene by catalytic gas phase oxidation and then producing acrylic acid from this acrolein by catalytic gas phase oxidation, or comprise the step of producing methacrylic acid from such as isobutylene by catalytic gas phase oxidation. Specific examples of the apparatus include reactors, absorbers, stripping columns, extraction columns, distillation columns, and their fittings such as heat exchangers, piping and tanks. In particular, it is preferred that reboilers of distillation columns in which (meth)acrylic acid is exposed to severe conditions are made of the nickel-chromium-iron alloy as specified in the present invention. The type of the reboiler is not particularly limited, but examples thereof include vertical shell-and-tube-type reboilers, horizontal shell-and-tube-type reboilers, and thin-film evaporators.

At least a part (particularly, a part coming into contact with (meth)acrylic acid) of the apparatus according to the present invention is made of the following nickel-chromium-iron alloy (A) or (B).

(A) A nickel-chromium-iron alloy with a molybdenum content of 3 to 20 mass %, but not including 3 mass %.

This alloy (A) contains the following components:
Nickel: 10 to 65 mass %
Chromium: 10 to 30 mass %
Iron: 4 to 70 mass %
Molybdenum: 3 to 20 mass % (but not including 3 mass %),
preferably 4 to 20 mass %
Copper: 0 to 7 mass %
Tungsten: 0 to 5 mass %
Nitrogen: 0 to 0.5 mass %

The balance may include such as carbon, silicon, manganese, phosphorous, or sulfur in the allowable range, for example, in the range included in conventional stainless steel. Furthermore, a trace of such as cobalt, vanadium, niobium, or tantalum may be contained.

Typical examples of this alloy (A) include SUS317J1, Hastelloy C-276 (produced by Mitsubishi Material), and NAS144M (produced by Nihon Yakin).

(B) A nickel-chromium-iron alloy with a molybdenum content of 1 to 4 mass % and a copper content of 0.5 to 7 mass %.

This alloy (B) contains the following components:
Nickel: 10 to 65 mass %
Chromium: 10 to 30 mass %

Iron: 4 to 70 mass %

Molybdenum: 1 to 4 mass %

Copper: 0.5 to 7 mass %, preferably 1 to 7 mass %

Tungsten: 0 to 5 mass %

Nitrogen: 0 to 0.5 mass %

The balance may include such as carbon, silicon, manganese, phosphorous, or sulfur in the allowable range, for example, in the range included in conventional stainless steel. Furthermore, a trace of such as cobalt, vanadium, niobium, or tantalum may be contained.

Typical examples of this alloy (B) include SUS329J1, SUS316J1, and SUS316J1L. In particular, SUS316J1 and SUS316J1L are preferably used.

Of the above alloys (A) and (B), the alloy (A) with a higher molybdenum content is more preferably used.

A part or the whole of the apparatus according to the present invention is made of the above alloy (A) or (B). Of course, the inner wall surface of the apparatus may be treated by conventional methods. Specifically, it is preferable that at least a part of the inner surface of the apparatus has an Ry, as prescribed in JIS B0601, of not more than 12.5, where Ry stands for maximum height of profile and where JIS stands for Japanese Industrial Standards.

The reason why the polymerization of (meth)acrylic acid can effectively be inhibited with the alloy (A) or (B) according to the present invention is not clear, but is considered to be as follows. In the case of the conventional stainless steel with a low molybdenum content (SUS316), its corrosion resistance is sufficient, but its surface is roughened by fine corrosion, and the liquid of (meth)acrylic acid resides on this roughened surface, so that the polymerization of (meth)acrylic acid easily occurs. In comparison, as to the alloy (A) or (B) according to the present invention, the surface roughening due to corrosion does not occur, therefore not only the residence of the liquid of (meth)acrylic acid, but also its polymerization can effectively be inhibited. Incidentally, the present invention is not limited by such a theoretical concept.

The production process according to the present invention for (meth)acrylic acid can be carried out under conventional conditions except that the apparatus of which at least a part is made of the above alloy (A) or (B) is used. In this process, of course, conventional polymerization inhibitors such as hydroquinone, phenothiazine, hydroquinone monomethyl ether, diphenylamine, copper dialkyldithiocarbamates, N-oxyl compounds and molecular-oxygen-containing gases may further be used.

(Effects and Advantages of the Invention):

The present invention enables the effective inhibition of the polymerization of (meth)acrylic acid by making at least a part of the production apparatus for (meth)acrylic acid out of the above alloy (A) or (B) and to therefore produce (meth)acrylic acid stably for a long period of time.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to the below-mentioned examples.

EXAMPLE 1

Crude acrylic acid containing high boiling point impurities (acrylic acid content=97.9 mass %, acrylic acid dimer content=1.3 mass %, others content=0.8 mass %) was continuously supplied into the column bottom of a distillation column (having a column diameter of 1.2 m and 20 dual-flow tray plates) with a condenser and a reboiler at a rate of 3,000 kg/h, and then distilled at a reflux ratio of 2 to recover acrylic acid from the column top at a rate of 2,700 kg/h (operating pressure=50 hPa). The material for the condenser, the distillation column, the dual-flow tray plates and the reboiler was NAS144M (produced by Nihon Yakin, molybdenum content=4.00 to 5.50 mass %). In addition, the inner surface of the apparatus was buffed so that-its Ry as prescribed in JIS B0601 would be 12.5.

Phenothiazine, as a polymerization inhibitor, was dissolved into the reflux liquid in a ratio of 300 ppm, and then introduced from the column top. In addition, into the reboiler, molecular oxygen was introduced in a ratio of 1 vol. % of the standard-state amount of the acrylic acid vapor as stripped in the reboiler.

After continuous operation for 100 days, the operation was stopped to check the inside of the apparatus. The degree of corrosion (by the year) was not more than 0.01 mm, and no deposition of the polymer was detected. Incidentally, the degree of corrosion (by the year) was calculated from the mass loss as determined by placing test pieces (50 mm×30 mm×3 mm) of NAS144M (which was the same material as that for the apparatus) into the apparatus (condenser, distillation column, reboiler), and then operating the apparatus continuously for 100 days, and then getting out the test pieces, and then measuring the mass of the test pieces.

EXAMPLE 2

Crude acrylic acid was distilled in the same manner as of Example 1 except that the material for the reboiler was changed to Hastelloy C-276 (produced by Mitsubishi Material, molybdenum content=15.0 to 17.0 mass %). After continuous operation for 100 days, the operation was stopped to check the inside of the apparatus. The degree of corrosion (by the year) in the reboiler was not more than 0.01 mm, and no deposition of the polymer in the reboiler was detected. The insides of the condenser and the distillation column were the same as those in Example 1. Incidentally, the degree of corrosion (by the year) in the reboiler was measured in the same manner as of Example 1 except that test pieces of Hastelloy C-276 (which was the same material as that for the reboiler) were placed into the reboiler.

EXAMPLE 3

Crude acrylic acid was distilled in the same manner as of Example 1 except that the material for the reboiler was changed to SUS316J1L (molybdenum content=1.20 to 2.75 mass %, copper content=1.00 to 2.5 mass %). After continuous operation for 100 days, the operation was stopped to check the inside of the apparatus. The degree of corrosion (by the year) in the reboiler was not more than 0.01 mm, but only a little deposition of the polymer in the reboiler was detected. The insides of the condenser and the distillation column were the same as those in Example 1. Incidentally, the degree of corrosion (by the year) in the reboiler was measured in the same manner as of Example 1 except that test pieces of SUS316J1L (which was the same material as that for the reboiler) were placed into the reboiler.

COMPARATIVE EXAMPLE 1

Crude acrylic acid was distilled in the same manner as of Example 1 except that the material for the reboiler was changed to SUS316 (molybdenum content=2.00 to 3.00 mass %, no copper content). After continuous operation for 100 days, the operation was stopped to check the inside of the apparatus. The degree of corrosion (by the year) in the reboiler was not more than 0.01 mm, but much deposition of the polymer in the reboiler was detected. Incidentally, the degree of corrosion (by the year) in the reboiler was measured in the same manner as of Example 1 except that test pieces of SUS316 (which was the same material as that for the reboiler) were placed into the reboiler.

Various details of the invention, may be changed without departing from its spirit not its scope. Furthermore, the foregoing description of the preferred embodiments according to the present invention is provided for the purpose of illustration only, and not for the purpose of limiting the invention as defined by the appended claims and their equivalents.

FIG. 1 shows a schematic view of an apparatus for producing (meth)acrylic acid. This apparatus includes a reactor 1, a reactor 2, an absorber 3, a stripping column 4, a condenser 5, a condenser 9, a condenser 13, an oil-water separation vessel 6, a distillation column 7, a distillation column 11, a distillation column 14, a reboiler 8, a reboiler 12, a vessel 10, a vessel 16, and a thin-film evaporator 15.

What is claimed is:

1. An apparatus for producing (meth) acrylic acid by catalytic gas phase oxidation, with said apparatus being selected from the group consisting of a reactor, an absorber, a stripping column, an extraction column, a distillation column, their fittings including heat exchangers, and reboilers off distillation columns, wherein said apparatus comprises a part that comes into contact with (meth)acrylic acid, and wherein said part comprises:
   (A) an alloy (A) comprising nickel, chromium and iron, with said alloy (A) having a molybdenum content of more than 3 mass % and not more than 20 mass %, with said alloy (A) minimizing polymerization of (meth)acrylic acid during production of (meth)acrylic acid; or
   (B) an alloy (B) comprising nickel, chromium and iron, with said alloy (B) having a molybdenum content of 1 to 4 mass % and a copper content of 0.5 to 7 mass %, with said alloy (B) minimizing polymerization of (meth)acrylic acid during production of (meth)acrylic acid.

2. An apparatus according to claim 1, wherein the apparatus comprises the distillation column.

3. An apparatus according to claim 1, wherein the apparatus comprises the reboiler of the distillation column.

4. An apparatus according to claim 1, of which at least a part of an inner surface of the apparatus has an Ry, as prescribed in JIS B0601, of not more than 12.5, where Ry stands for maximum height of profile and where JIS stands for Japanese industrial Standards.

5. An apparatus according to claim 1, wherein the alloy (A) further comprises copper in an amount of 0 to 7 mass %, tungsten in an amount of 0 to 5 mass %, and nitrogen in an amount of 0 to 0.5 mass %, and wherein said nickel is present in an amount of 10 to 65 mass %, said chromium is present in an amount of 10 to 35 mass %, and said iron is present in an amount of 4 to 70 mass %.

6. An apparatus according to claim 1, wherein the alloy (B) further comprises tungsten in an amount of 0 to 5 mass %, and nitrogen in an amount of 0 to 0.5 mass %, and wherein said nickel is present in an amount of 10 to 65 mass %, said chromium is present in an amount of 10 to 30 mass %, and said iron is present in an amount of 4 to 70 mass %.

7. An apparatus according to claim 1, wherein said apparatus further includes SUS 316 stainless steel comprising molybdenum in an amount of 2.0 to 3.0 mass % and copper in an amount of 0 mass %.

8. An apparatus according to claim 1, wherein said apparatus is the absorber.

9. An apparatus according to claim 1, wherein said apparatus is the heat exchanger.

10. A distillation column reboiler for distilling (meth) acrylic acid, comprising a portion coming into contact with (meth)acrylic acid, with said portion comprising:
   (A) an alloy (A) comprising nickel, chromium, and iron, with said alloy (A) having a molybdenum content of more than 3 mass % and not more than 20 mass %; or
   (B) an alloy (B) comprising nickel, chromium, and iron, with said alloy (B) having a molybdenum content of 1 to 4 mass % and a copper content of 0.5 to 7 mass %.

11. An apparatus according to claim 10, wherein the alloy (A) further comprises copper in an amount of 0 to 7 mass %, tungsten in an amount of 0 to 5 mass %, and nitrogen in an amount of 0 to 0.5 mass %, and wherein said nickel is present in an amount of 10 to 65 mass %, said chromium is present in an amount of 10 to 35 mass %, and said iron is present in an amount of 4 to 70 mass %.

12. An apparatus according to claim 10, wherein the alloy (B) further comprises tungsten in an amount of 0 to 5 mass %, and nitrogen in an amount of 0 to 0.5 mass %, and wherein said nickel is present in an amount of 10 to 65 mass %, said chromium is present in an amount of 10 to 30 mass %, and said iron is present in an amount of 4 to 70 mass %.

13. An apparatus according to claim 10, wherein said apparatus further includes SUS 316 stainless steel comprising molybdenum in an amount of 2.0 to 3.0 mass % and copper in an amount of 0 mass %.

14. An apparatus for producing (meth)acrylic acid by catalytic gas phase oxidation, comprising a portion coming into contact with (meth)acrylic acid, with the portion comprising:
   (A) an alloy (A) comprising nickel, chromium, and iron, with said alloy (A) having a molybdenum content of more than 3 mass % and not more than 20 mass %; or
   (B) alloy (B) comprising nickel, chromium, and iron, with said alloy (B) having a molybdenum content of 1 to 4 mass % and a copper content of 0.5 to 7 mass %.

15. An apparatus according to claim 14, wherein the alloy (A) further comprises copper in an amount of 0 to 7 mass %, tungsten in an amount of 0 to 5 mass %, and nitrogen in an amount of 0 to 0.5 mass %, and wherein said nickel is present in an amount of 10 to 65 mass %, said chromium is present in an amount of 10 to 35 mass %, and said iron is present in an amount of 4 to 70 mass %.

16. An apparatus according to claim 14, wherein the alloy (B) further comprises tungsten in an amount of 0 to 5 mass %, and nitrogen in an amount of 0 to 0.5 mass %, and wherein said nickel is present in an amount of 10 to 65 mass %, said chromium is present in an amount of 10 to 30 mass %, and said iron is present in an amount of 4 to 70 mass %.

17. An apparatus according to claim 14, wherein said apparatus further includes SUS 316 stainless steel comprising molybdenum in an amount of 2.0 to 3.0 mass % and copper in an amount of 0 mass %.

* * * * *

UNITED STATES PATENT AND TRADEMARK OFFICE
CERTIFICATE OF CORRECTION

PATENT NO.        : 6,966,973 B2
APPLICATION NO.   : 10/186569
DATED             : November 22, 2005
INVENTOR(S)       : Nakahara et al.

It is certified that error appears in the above-identified patent and that said Letters Patent is hereby corrected as shown below:

Title Page,

Please add the following:

-- (30)    Foreign Application Priority Data
Dec. 28, 1999   (JP) .......................................... 11-374113 --.

Signed and Sealed this

Fifth Day of May, 2009

JOHN DOLL
*Acting Director of the United States Patent and Trademark Office*